(12) United States Patent
Blaszczykiewicz et al.

(10) Patent No.: US 10,039,665 B2
(45) Date of Patent: Aug. 7, 2018

(54) MEDICAL HEADGEAR

(75) Inventors: Thomas Blaszczykiewicz, Orchard Park, NY (US); James V. Nutty, Buffalo, NY (US)

(73) Assignee: RESMED LIMITED, Bella Vista (AU)

( * ) Notice: Subject to any disclaimer, the term of this patent is extended or adjusted under 35 U.S.C. 154(b) by 1573 days.

(21) Appl. No.: 12/474,744

(22) Filed: May 29, 2009

(65) Prior Publication Data
US 2010/0000544 A1    Jan. 7, 2010

Related U.S. Application Data

(60) Provisional application No. 61/056,913, filed on May 29, 2008, provisional application No. 61/056,917, filed on May 29, 2008, provisional application No. 61/056,924, filed on May 29, 2008.

(51) Int. Cl.
| | |
|---|---|
| A62B 18/08 | (2006.01) |
| A62B 18/02 | (2006.01) |
| A61F 5/56 | (2006.01) |
| A61M 16/06 | (2006.01) |

(52) U.S. Cl.
CPC ........... *A61F 5/56* (2013.01); *A61M 16/0683* (2013.01); *Y10T 428/249921* (2015.04); *Y10T 428/249953* (2015.04); *Y10T 442/40* (2015.04)

(58) Field of Classification Search
CPC .... A61F 5/01; A61F 2262/12; B32B 2262/14; A42B 3/125; A61M 16/0683; A61M 25/02; A61M 16/00; A61M 16/06–16/0694; A62B 18/084
USPC .................................................. 128/207.17
See application file for complete search history.

(56) References Cited

U.S. PATENT DOCUMENTS

| | | | |
|---|---|---|---|
| 4,695,501 A * | 9/1987 | Robinson | 428/159 |
| 5,490,890 A | 2/1996 | Morrison | |
| 5,817,041 A * | 10/1998 | Bader | 602/23 |
| 6,019,101 A | 2/2000 | Cotner et al. | |

(Continued)

FOREIGN PATENT DOCUMENTS

| | | |
|---|---|---|
| CN | 1750853 | 3/2006 |
| CN | 101237902 | 8/2008 |

(Continued)

OTHER PUBLICATIONS

E.Navarro, J.A. Subirana, J.Puiggali, Polymer, Copyright @ 1997 Published by Elsevier Ltd, vol. 38 Issue 13, pp. 3429-3432.*

(Continued)

*Primary Examiner* — (Jackie) Tan-Uyen T Ho
*Assistant Examiner* — Ned T Heffner
(74) *Attorney, Agent, or Firm* — Nixon & Vanderhye P.C.

(57) ABSTRACT

A medical headgear fabric that includes, at least: (i) a skin-facing fabric layer; (ii) an outermost fabric layer; and (iii) a plastic or metal layer located between the fabric layers. Preferably these layers, as well as any additional layers that may be present in the fabric are thermoformed to form a substantially unitary fabric with at least a substantially laminate structure. Preferably, the fabric also includes a foam layer located between the fabric layers. Preferably, in embodiments with a layer (iii) of plastic, the plastic layer is in the form of a nylon, plastic strip. Preferably, in embodiments with a layer (iii) of metal, the metal layer is in the form of an aluminum strip.

27 Claims, 5 Drawing Sheets

(56) References Cited

U.S. PATENT DOCUMENTS

| | | | |
|---|---|---|---|
| 6,062,221 A * | 5/2000 | Brostrom et al. | 128/206.27 |
| 6,269,814 B1 | 8/2001 | Blaszczykiewicz et al. | |
| 6,470,886 B1 * | 10/2002 | Jestrabek-Hart | 128/207.11 |
| 6,494,207 B1 | 12/2002 | Kwok | |
| 6,805,117 B1 | 10/2004 | Ho et al. | |
| 6,861,379 B1 * | 3/2005 | Blaszczykiewicz | 442/373 |
| 6,907,882 B2 | 6/2005 | Ging et al. | |
| 7,047,972 B2 | 5/2006 | Ging et al. | |
| 7,188,620 B2 * | 3/2007 | Amarasinghe | 128/201.22 |
| 7,296,575 B1 * | 11/2007 | Radney | 128/207.11 |
| 7,318,437 B2 | 1/2008 | Gunaratnam et al. | |
| 7,509,958 B2 | 3/2009 | Amarasinghe et al. | |
| 8,286,634 B2 | 10/2012 | Madaus et al. | |
| 8,356,602 B2 | 1/2013 | Crocetti | |
| 2003/0056785 A1 | 3/2003 | Narihiko et al. | |
| 2003/0118808 A1 * | 6/2003 | Canamero et al. | 428/318.4 |
| 2004/0025882 A1 | 2/2004 | Madaus et al. | |
| 2004/0149280 A1 | 8/2004 | Semeniuk | |
| 2006/0081250 A1 | 4/2006 | Bordewick et al. | |
| 2007/0181135 A1 | 8/2007 | Baker | |
| 2007/0264462 A1 * | 11/2007 | Covelli et al. | 428/43 |
| 2008/0047560 A1 * | 2/2008 | Veliss et al. | 128/206.24 |
| 2008/0060745 A1 * | 3/2008 | Lau | 156/182 |
| 2009/0107514 A1 * | 4/2009 | Winningham | 128/857 |

FOREIGN PATENT DOCUMENTS

| | | |
|---|---|---|
| JP | 8-57055 | 3/1996 |
| JP | 2004-351040 | 12/2004 |
| JP | 2011-52173 | 7/2011 |
| WO | WO 2006/130903 A1 | 12/2006 |
| WO | WO 2008030831 A2 * | 3/2008 |

OTHER PUBLICATIONS

PCT Search Report, dated Jan. 12, 2010, from International Counter Part Application No. PCT/US2009/045669.
International Preliminary Report on Patentability for corresponding PCT Application PCT/US2009/045669, dated Nov. 30, 2010, 7 pages.
Office Action issued in a corresponding Chinese Application No. 200980119660.9 (dated Jan. 7, 2013) with English translation thereof.
Second Office Action issued in corresponding Japanese Application No. 2011-511854 dated Jan. 7, 2014 with English-language translation.
Further Examination Report dated May 7, 2013 issued in corresponding New Zealand Application No. 589901.
Notification of the Second Office Action issued in a corresponding Chinese Application No. 200980119660.9 dated Sep. 24, 2013.
Patent Examination Report No. 1 dated Feb. 1, 2013 in corresponding Australian Application No. 2009256467 (4 pages).
First Examination Report dated May 8, 2013 issued in corresponding Australian Application No. 610179 (2 pages).
Notice of Reasons for Rejection issued in corresponding Japanese Application No. 2011-511854 (with English-language translation) dated Jun. 4, 2013.
Australian Patent Examination Report No. 2 dated Feb. 12, 2014 in corresponding Australian Patent Application No. 20092564467.
Notice of Reasons for Rejection dated Nov. 4, 2014 issued in corresponding Japanese Application No. 2011-511854 with English translation (6 pages).
Further Examination Report dated Nov. 28, 2014 issued in corresponding New Zealand Application No. 610179 (2 pages).
Intellectual Property Office of New Zealand—Patent Decisions—Abbot Laboratories [2003] NZIPOPAT 16 (Aug. 11, 2003), http://www.nzlii.org/nz/cases/NZIPOPAT/2003/16.html, (5 pages).
Armstrong-Kropp Development Corporation's Applications [1974] R.P.C., pp. 268-271.
Extended Search Report dated Dec. 15, 2014 issued in corresponding European Application No. 09759117.6 (6 pages).
Third Office Action dated Apr. 17, 2014 in corresponding Chinese Patent Application No. 200980119660.9 (with English-language translation thereof).
Further Examination Report dated Aug. 22, 2014 in New Zealand Application No. 610179 (1 page).
Decision of Rejection dated Oct. 10, 2014 issued in corresponding Chinese Application No. 200980119660.9 with English translation (17 pages).
Decision of Commissioner dated Sep. 15, 2015, in a corresponding New Zealand Application No. 610179 (10 pages).
Notice of Opposition to Grant of Patent filed Sep. 29, 2015, in a related New Zealand Application No. 616559 (4 pages) citing U.S. Pat. No. 7,210,481.
Patent. Examination Report No. 2 dated Sep. 16. 2015, in a related Australian Application No. 2014201197 (2 pages).
Further Examination Report dated Jul. 7, 2015 in a corresponding New Zealand Application No. 701499 (2 pages).
Notice of Opposition to Grant of Patent filed Apr. 24, 2015 in New Zealand Patent Application No. 610179 (2 pages).
A First Office Action issued in a related Japanese Application No. 2015-021033 (2 pages), and an English translation thereof (2 pages), citing Japanese Patent Application No. 2011-539848 (60 pages) (for which PCT Publication No. WO 2010/066004 is a corresponding English language application) (82 pages).
Notification of Reexamination dated Mar. 16, 2016 in a corresponding Chinese Application No. 200980119660.9 (7 pages) and an English translation thereof (10 pages).
Further Examination Report dated Feb. 23, 2016 in a related New Zealand Application No. 706870 (2 pages).
First Office Action dated Apr. 13, 2016 in a corresponding Chinese Application No. 201510036005.4 (9 pages), and an English translation thereof (11 pages).
A Decision of Rejection dated Apr. 26, 2016 in a corresponding Japanese Application No. 2015-117246 (4 pages), and an English translation thereof (5 pages).
A Notice of Reexamination dated May 11, 2016 in a related Chinese Application No. 200980149789.4 (8 pages), and an English translation thereof (12 pages), citing U.S. Pat. No. 5,416,924 (SIMS).
Office Action dated Jan. 26, 2017, in a related U.S. Appl. No. 14/601,316 (42 pages), citing U.S. Pat. Nos. 7,562,658 and 3,424,633 and U.S. Pat. Nos. 2004/0083534, 2006/0081252, and 2010/0000544.
Petition for Inter Partes Review of U.S. Pat. No. 8,950,404, submitted Aug. 2, 2017, in the United States Patent and Trademark Office before the Patent Trial and Appeal Board, *Fisher & Paykel Healthcare Limited, Petitioner, v. ResMed Limited, Patent Owner*, Case No. IPR2017-01905 (106 pages), citing U.S. Pat. No. 2,126,755, U.S. Pat. No. 2006/0118117, PCT Publication Nos. WO 2007/006089 (49 pages) and WO 2008/068966 (35 pages) with Certified English Translation (24 pages), and Decision on Institution of Inter Partes Review Pending Case IPR2017-00340, Paper No. 8, dated May 16, 2017 (54 pages) (copies attached, excluding U.S. patents and U.S. patent publications).
A Final Office Action dated Aug. 24, 2017, in a related U.S. Appl. No. 14/511,933 (12 pages), citing U.S. Pat. No. 4,409,163.
Notification of Reexamination dated Jul. 12, 2016 in a corresponding Chinese Application No. 200980119660.9 (7 pages), and an English translation thereof (12 pages).
Patent Exam Report No. 1 dated Nov. 28, 2016 in a related Australian Application No. 2016201534 (2 pages), citing Canadian Patent Application No. 2 671 591 (32 pages), and PCT Publication Nos. WO 2006/072128 (25 pages) and WO 2000/050122 (33 pages) (copies attached).
Petition for Inter Partes Review of related U.S. Pat. No. 8,950,404, filed Nov. 28, 2016 in the U.S. Patent and Trademark Office, Patent Trial and Appeal Board, *Fisher & Paykel Healthcare Limited v. Resilled Limited* (102 pages), citing U.S. Pat. No. 8,950,404, PCT Publication No. WO 2004/041341 (35 pages), U.S. Pat. No. 3,424,633, PCT Publication No. WO 2002/047749 (28 pages), PCT Publication No. WO 2010/0066004 (82 pages), Australian Patent Application No. 2008-906390 (30 pages), Australian Patent Appli- (56) References Cited

OTHER PUBLICATIONS cation No. 2009-900327 (42 pages), Australian Patent Application No. 2009-902731 (57 pages), Australian Patent Application No. 2009-904236 (61 pages), U.S. Appl. No. 60/842,741 (34 pages), U.S. Pat. No. 2011/0072553, Declaration of Richard Lordo, P.E., In Support of Petition for Inter Partes Review of U.S. Pat. No. 8,950,404 (dated Nov. 28, 2016 (214 pages)), Excerpts from the U.S. Patent and Trademark Office File History of U.S. Pat. No. 8,950,404 (formerly U.S. Appl. No. 12/998,420) (666 pages), Answer of ResMed Corp. to Complaint for Patent Infringement and Counterclaims, *Fisher & Paykel Healthcare Limited v. ResMed Corp.*, United States District Court for the Southern District of California, Case No. 16CV2068 GPC WVG dated Sep. 7, 2016 (94 pages), U.S. Pat. No. 6,119,694, PCT Publication No. WO 2009/059353 (121 pages), U.S. Pat. No. 2009/0044808, PCT Publication No. WO 2009/026627 (35 pages), PCT Publication No. 2009/052560 (183 pages), U.S. Pat. No. 7,210,481, U.S. Pat. No. 8,443,807, 8,479,741, 8,186,345, 8,453,641, 9,265,902, 8,550,072, 8,091,547, 7,111,624, 6,398,197, 8,944,061, 8,960,196, 9,027,556, 9,119,931, 9,242,062, and 9,381,316 (copies of all documents attached, excluding U.S. Patents and U.S. Patent Application Publications).

Decision of Reexamination dated Nov. 14, 2016, in a related Chinese Application No. 2016110900258470 (24 pages), and an English translation thereof (34 pages), citing U.S. Pat. No. 5,416,924.

Decision of Reexamination dated Nov. 23, 2016, in a corresponding Chinese Application No. 2016111800561610 (15 pages), and an English translation thereof (18 pages).

A Second Notice of Opposition to Grant of Patent (Section 21) dated Jun. 8, 2017 (2 pages), citing U.S. Pat. No. 3,295,529, 6,739,427 and 7,210,481 and PCT Publication Nos. WO 2002/047749 and WO 2004/041341; a Statement of Case dated Jun. 8, 2017 (25 pages), and a Deadline for Counterstatement issued Jun. 15, 2017 (2 pages), citing PCT Publication No. WO 2010/066004, in a related New Zealand Application No. 706870 (copies attached, excluding U.S. patents).

A First Examination Report dated Dec. 4, 2017, in a corresponding New Zealand Patent Application No. 737024 (3 pages).

A Notice of Allowance dated Jan. 15, 2018, in a related Japanese Application No. 2016-036831 (3 pages), citing Japanese Patent Publication JPU55-16140 (8 pages, with abstract).

A Notice of Opposition to Grant of Patent (Section 21) (2 pages) and an Application Under Regulation 168 for Extension of Time (1 page) filed Mar. 28, 2017, in a related New Zealand Application No. 706870, citing U.S. Pat. No. 3,295,529 and 7,210,481, and PCT Publication Nos. WO 2002/047749 (28 pages) and WO 2004/041341 (35 pages) (copies of all documents attached, excluding U.S. Patents and U.S. Patent Application Publications).

Office Action dated Oct. 18, 2016 in a related German Application No. 103 52 608.0 (13 pages), and an English translation thereof (10 pages), citing German Patent No. 100 35 946 (16 pages, including Abstract), French U.S. Pat. No. 2 658 725 (14 pages, including Abstract), U.S. Pat. No. 5,542,128 and 5,720.715, Turbocast 3M Data Sheet, URL: http://www.servoprax.de/shop/unser-angebot/medical-products/verbandmittel/schienen-und-orthesen/turbocast-3m , downloaded Jan. 18, 2016 (1 page), and Turbocast—Niedertemperatur—Thermoplast Data Sheet, URL: http://www.orthopaedie-bedarf.com/rel/pages/produkte/produkte_a_z/turbocast.php?id=03,01,07 , downloaded Oct. 18, 2016 (1 page) (copies attached).

An Office Action dated Jan. 16, 2017, in a related Japanese Application No. 2016-036831 (3 pages), and an English translation thereof (4 pages), citing Japanese Patent Publication Nos. JP-T-2008-502380 (65 pages, with Abstract) , JP-A-2000-102624 (6 pages, including Abstract), JP-A-2004-000571 (149 pages, with Abstract), JP-A-2000-254229 (17 pages, including Abstract), Microfilm of Japanese Registration No. S53-98392 (7 pages), and U.S. Pat. No. 2003/0051732 (copies of all documents attached, excluding U.S. Patents and U.S. Patent Application Publications).

An Office Action dated Feb. 4, 2017, in a related Chinese Application No. 201510026138.3 (9 pages), and an English translation thereof (9 pages), citing Chinese Publication No. CN 101143029 (22 pages, with Abstract), European Patent No. EP 1919724 (24 pages), PCT Publication No. WO 2004/012803 (51 pages) (copies of all documents attached, excluding U.S. Patents and U.S. Patent Application Publications).

A Communication of a Notice of Opposition dated Jan. 5, 2017, in a related European Application No. 09831318.2 (60 pages), citing Exhibit N2—European Patent No. EP 2 373 368 (2 pages, including Abstract), Exhibit N3—PCT Publication No. WO 2010/066004 (82 pages), Exhibit N4—"Feature analysis of claim 1of the opposed patent" (1 page), Exhibit D1b—"Declaration of Christopher Earl Nightingale", dated Dec. 15, 2016 (8 pages), Exhibit D1c—"Design drawing of the headgear for the FlexiFit 431 mask (Revision D), dated May 11, 2006 (1 page), Exhibit D1d—"Design drawing of the headgear for the FlexiFit 431 mask (Revision E), dated Oct. 27, 2009 (1 page), Exhibit D1e—"Declaration of Olivia Allan", dated Dec. 15, 2016 (10 pages), Exhibit D2—U.S. Pat. No. 2004/0112377, Exhibit D3—U.S. Pat. No. 6,470,886, Exhibit D6—PCT Publication No. WO 2000/074758 (40 pages), Canadian U.S. Pat. No. 2 671 591 (32 pages), PCT Publication No. WO 2008/030831 (27 pages) (copies of all documents attached, excluding U.S. Patents and U.S. Patent Application Publications).

Extended European Search Report dated Aug. 19, 2016, in a related European Application No. 16159937.8 (8 pages), citing U.S. Pat. Nos. 2004/0067333, 2007/0186931, and 2004/0073989.

\* cited by examiner

MEDICAL HEADGEAR

The present application claims priority to the following U.S. provisional patent applications: Ser. No. 61/056,924 filed on May 29, 2008, Ser. No. 61/056,917 filed on May 29, 2008, and Ser. No. 61/056,913 filed on May 29, 2008, all of the foregoing patent-related document(s) are hereby incorporated by reference herein in their respective entirety(ies).

BACKGROUND OF THE INVENTION

1. Field of the Invention

The present invention relates to medical headgear fabrics and more particularly to a headgear for treatment of sleep apnea.

2. Description of the Related Art

Figure 1:
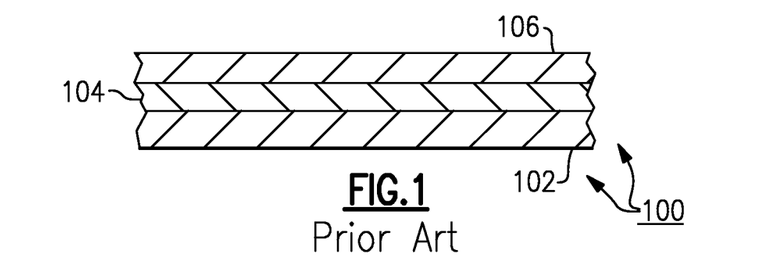
FIG. 1 is a partial cross-sectional view of a prior art medical headgear fabric.

Medical headgear for the treatment of respiratory conditions such as sleep apnea vary depending upon the nature and severity of the condition. In some conventional sleep apnea headgear designs, the headgear is fabricated of material having an intermediate rigidity, somewhere between pliable and bendable, whereby this rigidity is not "rigid" as defined by the Definitions set forth hereinafter. FIG. 1 shows an exploded view partial cross-section for one conventional sleep apnea headgear fabric 100, having three layers: (i) an outer nylon-LYCRA® layer 102; (ii) a breathable foam layer 104; and (iii) a skin-facing nylon-LYCRA® layer 106. The three layers 102, 104, 016 are flame laminated to form the three layer laminate shown (in exploded form) in FIG. 1.

Conventionally, headgear 100 is made by flame lamination. Flame lamination is a process used, typically in the textile industry, to permanently join fabrics and/or foam/neoprene to provide functionality for specific applications. More specifically, a polyurethane (PU) foam and two nylon/spandex blends form a three layer composite. The PU is fed into one side of the flame lamination machine at the same one of the fabrics is also fed in. The top surface of the foam is melted by direct flame contact to generate a tacky condition. The melted foam and fabric are then fed through a compression roller to squeeze the two materials together forcing the melted foam into the pores of the fabric. As it cools a bond is formed. This process is then repeated to bond the other fabric to the foam.

Thermoforming is a conventional process used to make laminate products, such as shoe insoles, but it is not believed to be conventionally used to make medical headgear fabrics and/or sleep apnea headgear fabrics.

U.S. Pat. No. 6,019,101 ("Cotner") discloses a nasal mask for treatment of sleep apnea. The Cotner mask includes a strap made from an elastically compliant material and a plastically deformable nose clip. The deformable nose clip may be manufactured from thin aluminum.

U.S. Pat. No. 6,269,814 ("Blaszczykiewicz") discloses a sleep apnea headgear including a chinstrap made from a stretchable, breathable, laminated neoprene substitute. The inner surface of the chinstrap is made from LYCRA® fabric. The outer surface of the chinstrap is made of UBL loop material.

U.S. Pat. No. 6,470,886 ("Jestrabek-Hart") discloses a headgear for treating sleep apnea including two panels. Each panel includes the following layers: (i) a skin-facing layer of soft, flexible cloth, pleasant to the touch; (ii) a plastic layer (ear encircling region only); (iii) soft flexible foam layer; and (iv) cloth outside surface layer. Although it is not immediately clear, it appears that the cloth outside surface layer, layer (iv), may be either covered, partially covered and/or replaced by a layer of material made of hook-and-loop fastener fabric (specifically, the hook side). As shown in FIG. 5 of Jestrabek-Hart, the Jestrabek-Hart headgear fabric has foam on only one side of its plastic layer. This construction may allow the plastic layer to tear through the outer fabric. Also, this construction will have a low degree of softness on the side of the plastic layer that has no foam.

U.S. Pat. No. 6,805,117 ("Ho") discloses a headgear including mesh-like panels(s) and a rear joint piece. The panels(s) are made from a nylon-LYCRA® blend. The rear joint piece is made from LYCRA® laminated foam or neoprene.

U.S. Pat. No. 7,047,972 ("Ging") discloses a respiratory mask including yokes and straps. The straps are made of laminated fabric and foam. Ging discloses that one commercially available material is "Beath-O-Prene"™ manufactured by Accumed, Inc. USA. The yokes are attached to the straps and are made of somewhat rigid plastic, such as nylon or polypropylene. It is noted that the yokes of the Ging mask are attached to the outside of the straps and not embedded within the laminate structure of the strap itself. It is believed that the Ging fabric requires separate attachment mechanisms such as sewing or clamping to secure its embedded plastic. Also, Ging is directed to a mask, and not a headgear or a sleep apnea headgear.

US patent application 2006/0081250 ("Bordewick") discloses a nasal mask includes a mask holder and a stabilizing band. The mask holder is made out of rigid or semi-rigid material, such as glass-filled nylon.

US patent application 2007/0181135 ("Baker") discloses a headgear assembly to treat sleep apnea. The Baker assembly includes a crown strap and a chin strap. The chin strap and crown straps are made of a breathable, elastic foam material laminated on both sides with a soft, moisture-wicking fabric. The outside fabric includes LYCRA® spandex and an anti-microbial agent, such as silver.

Description Of the Related Art Section Disclaimer: To the extent that specific publications are discussed above in this Description of the Related Art Section, these discussions should not be taken as an admission that the discussed publications (for example, published patents) are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section, they are all hereby incorporated by reference into this document in their respective entirety(ies).

BRIEF SUMMARY OF THE INVENTION

Embodiments of the present invention are directed to a medical headgear fabrics that include, at least: (i) a skin-facing fabric layer; (ii) an outermost fabric layer; and (iii) a layer of rigid material such as a "rigid" (see DEFINITIONS section) plastic material located between the fabric layers. Preferably these layers, as well as any additional layers that may be present in the fabric are thermoformed to form a substantially unitary fabric with at least a substantially laminate structure. Preferably, the fabric also includes a foam layer located between the fabric layers. Preferably, in embodiments with a layer (iii) of plastic, the plastic layer is in the form of a nylon, plastic strip.

Various embodiments of the present invention may exhibit one or more of the following objects, features and/or advantages:

(1) lamination by thermoforming to produce a thicker, more comfortable shape in the headgear made with the headgear fabric of the present invention;

(2) lamination by thermoforming to produce a headgear made with the headgear fabric of the present invention that more naturally conforms to the roundness of the human head;

(3) use of a metal layer in the headgear fabric to provide clearance from the patient's face;

(4) use of a metal layer in the headgear fabric to provide comfort to the patient's face;

(5) use of a rigid plastic layer to reduce or eliminate bulkiness in the headgear;

(6) use of a rigid plastic layer and/or a metal layer to replace external plastic parts for making connections to a breathing mask portion of the headgear;

(7) use of a rigid plastic layer and/or a metal layer to replace separate nylon rigidizers and/or yokes;

(8) use of a rigid plastic layer, preferably unitarily formed with the fabric, to reduce complexity of the assembly;

(9) use of a rigid plastic layer, preferably unitarily formed with the fabric, to reduce potential for the assembled fabric to disassemble;

(10) use of a rigid plastic layer, preferably unitarily formed with the fabric, to making a cleaner looking headgear with a more appealing visual appearance;

(11) use of a rigid plastic layer to add straight-ahead stiffness to the strap arm;

(12) use of a metal layer to enhance adjustability of the headgear; and/or (13) improved rigidity, especially in strap arm sections, helps hold a sleep apnea headgear tightly enough against the face so that the amount of pressurized air escaping along the skin is reduced or eliminated.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

I. Headgear Fabric Structures

As will be appreciated, embodiments of the present invention provide headgear fabric and devices fabricated of materials that exhibit comfort and flexibility to the wearer, while concurrently providing stability and integrity to the headgear device.

Figure 2:
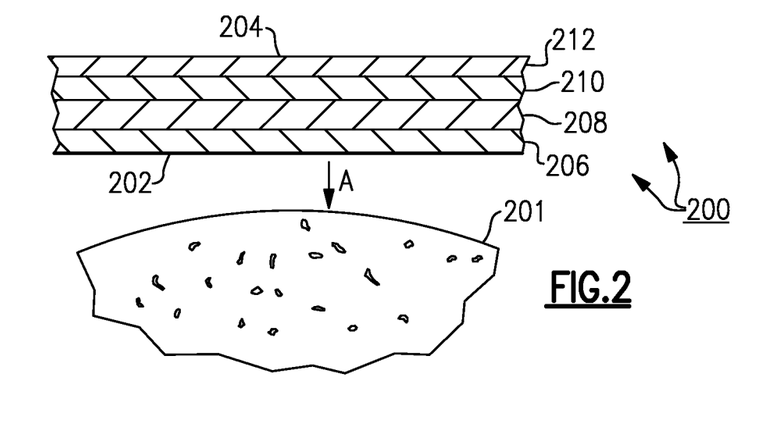
FIG. 2 is a partial cross-sectional view of a first embodiment of a medical headgear fabric according to the present invention.

Embodiments of the headgear are fabricated of a variety of layers of materials. Depending on the section or part of the headgear, the layers may or may not vary. Reference is made to FIG. 2 (not to scale), which shows a medical headgear fabric 200 including: a skin-facing fabric layer 206; a foam layer 208; a layer of rigid material 210; and an outer fabric layer 212. The skin-facing fabric layer includes skin-facing surface 202 (reference numeral 201 designates the skin, scalp or other portion of the patient that this fabric is intended to face or contact). The skin facing layer may be fabricated of any soft, fabric that is comfortable to the skin. The fabric may also exhibit stretch, elasticity, and/or wicking properties. Examples include, but are not limited to a nylon-LYCRA® blend, and microfiber knit fabric. The primary benefit of this layer is provide minimal friction with the person's skin. It is preferable that the knit fabric is porous and allows airflow to reduce perspiration. The skin-facing fabric may be treated with a chemical that promotes wicking, i.e., transportation of moisture, through to the next layer of the assembly.

The foam layer 208 provides cushioning and is preferably breathable, aiding in allowing moisture to move away from the skin toward the outside atmosphere by means of capillary attraction. The foam may be fabricated of a cellular, stretch-elastomer foam such as that described above for section 104, including but not limited to polyurethane foam.

The layer of rigid material 210 is any rigid material that provides integrity to the structure without the need for an external support or structure (such as rigidizers or yokes that are typically applied to similar structures on the external surface). The material may be any plastic, composite, metal, or ceramic material having enough strength to provide integrity to the structure, but also allows for some flexibility. Examples of materials include, but are not limited to, thermoplastic and fiber reinforced thermoplastic materials. Examples of thermoplastic materials include, but are not limited to, polyamides. Examples of polyamides include, but are not limited to, nylon 6 and nylon 12.

The rigid material 210 may be smaller in dimensions (i.e., the perimeter) than the dimensions of the layers it is juxtaposed or those layers positioned over or under thereto, i.e, layers 206, 208, 212, such that it can be centered in the assembly so that its sharp edges do not extend past the edge of the assembled structure, causing irritation to the person's skin. This rigid material provides a degree of stiffness to the assembly, particularly to the strap arm sections of a headgear device, to provide proper and appropriate placement of the device on the person's face and crown, as further described below in the Headgear Geometry section The outer fabric layer 212 includes outer surface 204 and may be a material similar to material used to fabricate layer 206 such as a nylon-LYCRA® blend, or microfiber knit fabric. It may further include an attachment means such as a series of small loops that provide a vehicle for engagement with a hook material to create the force that holds the headgear in place on the person. Structure 200 is merely exemplary and may include additional layers or layers disposed in a different order than shown in FIG. 2. For example, the order of layers 208 and 210 may be reversed.

It is preferable that the layers are thermoformed or thermoset together as further described below, to provide a finished product having only one seam or edge that is located away from the skin, on the outer fabric layer 212, to reduce any opportunity for skin irritation. Although thermoforming is preferable, the embodiments herein are not limited to this fabrication process and some variations may include some or all of the adjacent layers not being laminated to each other at all. Also, in embodiments where all of the adjacent layers are laminated together to form a unitary structure, other lamination processes may be used such as flame lamination.

Fabric 200 has good straight-ahead stiffness which means that the plastic layer helps direct certain sections of the headgear (for example, strap arm sections) in a specific direction, which can help facilitate assembly of medical headgears using fabric 200 to a face mask, such as a sleep apnea headgear face mask. This can obviate the need for a large of amount of different-sized headgear in order to accommodate a larger range of patient head sizes. Although not limited to any particular section of the headgear, it is preferable that a layered structure such as fabric 200 be used in the strap arm sections of the headgear, discussed further below under the Headgear Geometry section.

Figure 3:
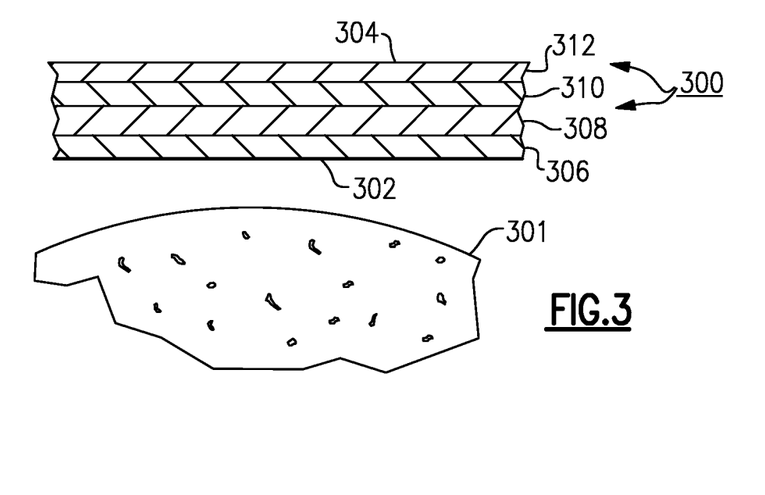
FIG. 3 is a partial cross-sectional view of a second embodiment of a medical headgear fabric according to the present invention.

FIG. 3 (not to scale) shows a medical headgear fabric 300 including: a skin-facing fabric layer 306; a foam layer 308; a metal layer 310; and an outer fabric layer 312. The skin-facing fabric layer 306 includes skin-facing surface 302 (reference numeral 301 designates the skin, scalp or other portion of the patient that this fabric is intended to face or contact) and can be fabricated of any soft fabric as indicated above for layer 206. The foam layer 308 is preferably breathable and may be fabricated of the same material discussed above in connection with layer 208. The metal layer 310 is preferably made of aluminum, and even more preferably made of galvanized aluminum. The outer fabric layer 312 includes outer surface 304 and is preferably made of similar materials as used to fabricate layer 212 above. As stated above for fabric or structure 200, the order of layers in fabric or structure 300 may also be reversed, such as layers 308 and 310. Also additional layers may be present.

As with structure or fabric 200, it is preferable that the layers of structure or fabric 300 are thermoformed or thermoset together as further described below, to provide a finished product having only one seam or edge that is located away from the skin, on the outer fabric layer 312 or on surface 304, to reduce any opportunity for skin irritation. Although thermoforming is preferable, the embodiments herein are not limited to this fabrication process and some variations may include some or all of the adjacent layers not being laminated to each other at all. Also, in embodiments where all of the adjacent layers are laminated together to form a unitary structure, other lamination processes may be used such as flame lamination.

Fabric 300 has good moldability. The metal layer helps: (i) fewer sizes of headgears accommodate a larger range of patient head sizes; and (ii) create clearances for comfort and spacing.

Figure 4:
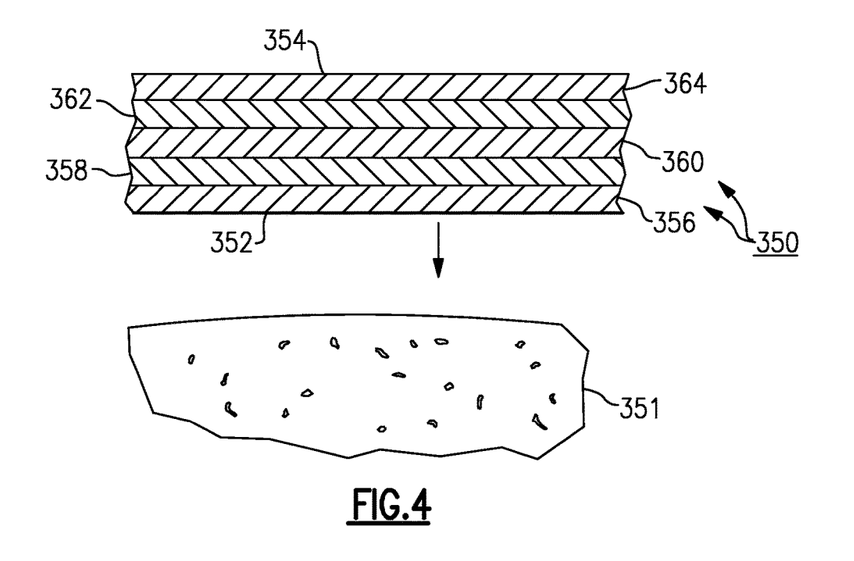
FIG. 4 is a partial cross-sectional view of a third embodiment of a medical headgear fabric according to the present invention.

FIG. 4 (not to scale) shows a medical headgear fabric 350 including: a skin-facing fabric layer 356; a foam layer 358; a metal layer 360; a rigid plastic layer 362 and an outer fabric layer 364. The skin-facing fabric layer includes skin-facing surface 352 (reference numeral 351 designates the skin, scalp or other portion of the patient that this fabric is intended to face or contact). The outer fabric layer 354 includes an outer fabric surface 354. The materials used for layers 356, 358, 360, 362 and 364 may be the same as or similar to those materials used in the fabrication of fabrics 200 and 300, where like sections can use the same or similar fabric, as discussed above.

Figure 5:
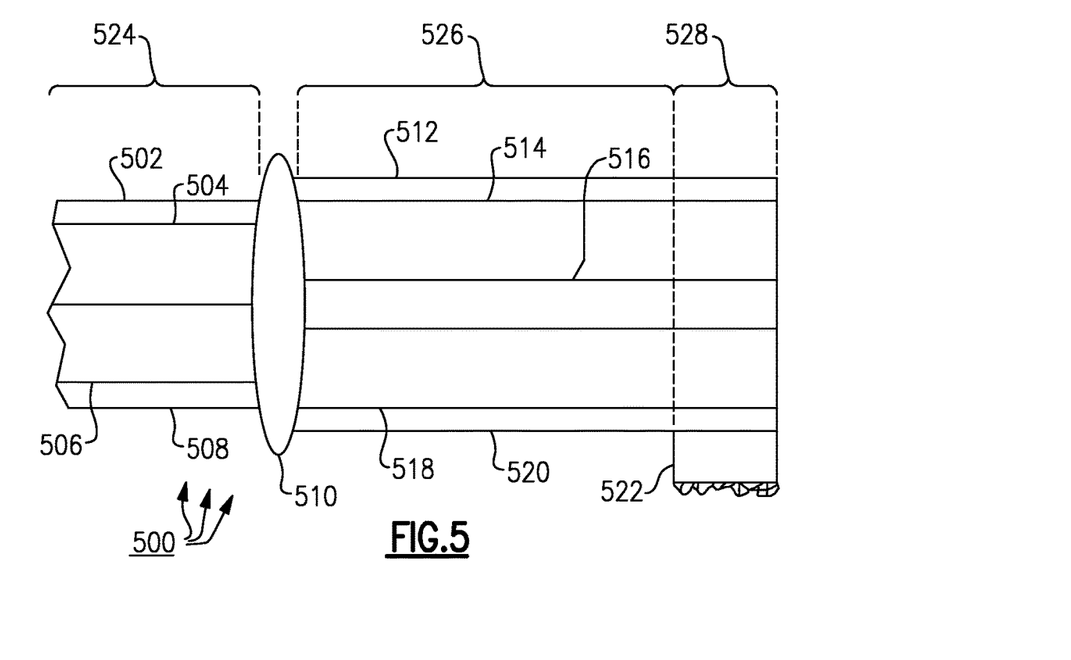
FIG. 5 is a partial cross-sectional view of a second embodiment of a sleep apnea headgear according to the present invention.

FIG. 5 shows a partial cross section of a headgear 500 including a crown section 524 and a strap section 526. Crown section 524 includes: a first crown section layer 502; a second crown section layer 504; a third crown section layer 506; and a fourth crown section layer 508. Joint 510 connects crown section 524 to strap section 526. Strap section 526 includes a first strap arm section layer 512; a second strap arm section layer 514; a third strap arm section layer 516; a fourth strap arm section layer 518; a fifth strap arm section layer 520; and a fastener layer 522. FIG. 5 also shows where the layers are located with respect to the headgear sections 524, 526, 528 shown in FIG. 6.

First crown section and fourth crown section layers 502 and 508, respectively, are preferably made of soft, stretchy fabric, the same as or similar to those materials discussed above or fabrics/structures 200, 300 and 400. Alternatively, some or all of the fourth crown section layer 508 may be made of fastener material, such as hook and loop fastener material, in order to facilitate attachment of other components to the headgear, such as a sleep apnea face mask (not shown). Second crown section layer 504 is preferably made of relatively high density foam, such as 101b density foam. Third crown section layer 506 is preferably made of relatively low density foam, such as 71b density foam.

First strap arm section and fifth strap arm section layers 512 and 520, respectively, are preferably made of soft, stretchy fabric. Alternatively, some or all of the fifth crown section layer may be made of fastener material, such as hook and loop fastener material, in order to facilitate attachment of other components to the headgear, such as a sleep apnea face mask (not shown). Under this alternative, fastener section 528 with fastener layer 522 may no longer be needed because the fastener fabric would already be present as the fifth layer. Second and fourth strap arm section layers 514, 518, respectively, are preferably made of relatively low density foam, such as 71b density foam. Third strap arm section layer 516 is a rigid material such as a rigid plastic layer, as discussed above in connection with fabric 200. Alternatively, or additionally, this layer 516 could be a metal, ceramic or composite layer as discussed above in connection with fabric 300.

The thickness, strength and hardness of each of the layers discussed above, may vary depending on the size and strength needed for the particular headgear device.

II. Overall Headgear Geometry

The medical headgear fabrics discussed above may be used in a wide variety of geometrically shaped headgear designs. In some preferred embodiments of the present invention, different fabrics, with different laminate structures, are used for different sections of the headgear.

Figure 6:
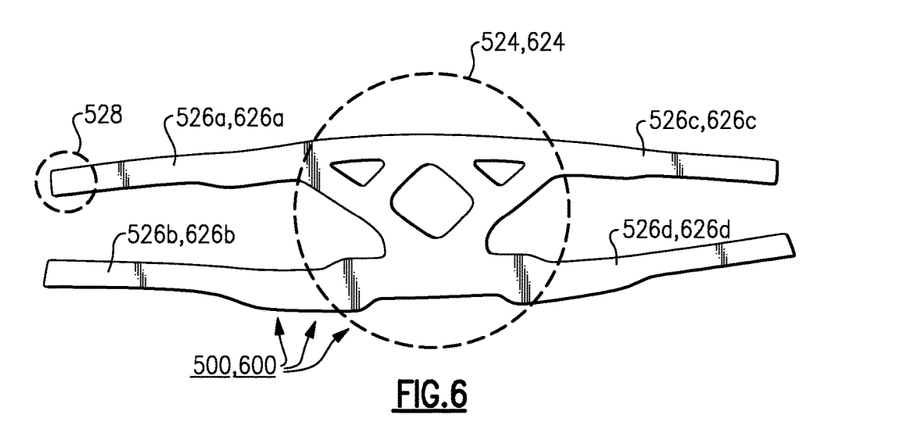
FIG. 6 shows a top orthographic view of a sleep apnea headgear overall geometry corresponding to both first and second sleep apnea headgear embodiments according to the present invention.

FIG. 6 shows a top orthographic view of a sleep apnea headgear overall geometry common to a first embodiment 500 and a second embodiment 600 of two exemplary sleep apnea headgears according to the present invention. As shown in FIG. 6, headgear 500 includes: a crown section 524; four strap arm sections 526a,526b,526c,526d; and a fastener section 528. As shown in FIG. 6, headgear 600 includes: a crown section 624; and four strap arm sections 626a,626b,626c,626d.

The main difference between headgear 500 and headgear 600 is that headgear 500 uses fabric 300 in its strap arm sections, while headgear 600 uses fabric 200 in its strap arm sections. Although this overall geometry 500, 600 is preferred, the use of the medical device headgear fabrics according to the present invention is not necessarily limited to what is shown in FIG. 6. This headgear geometry design, including strap arms and a crown section, is sometimes be referred to as a 3D headgear because it has multiple sections, with different sections having different thicknesses.

Figure 7:
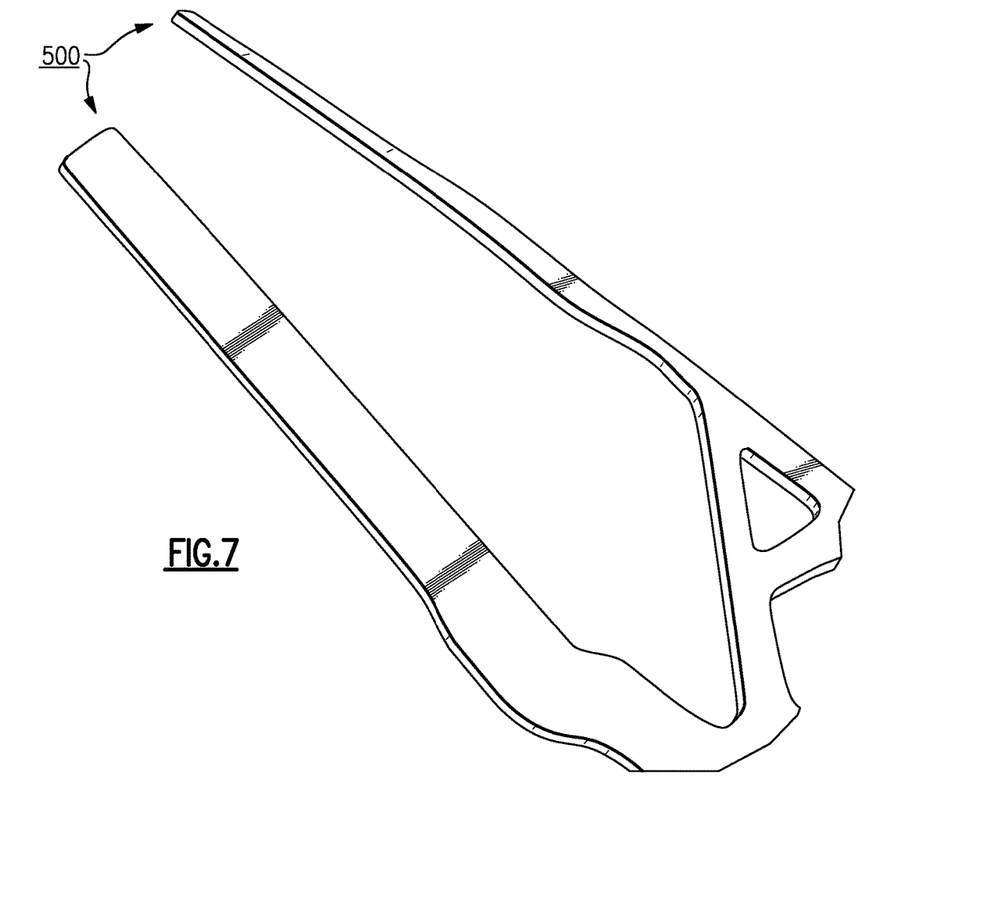
FIG. 7 shows a perspective view of the first embodiment of the sleep apnea headgear as it is being manipulated by a person.
Figure 8:
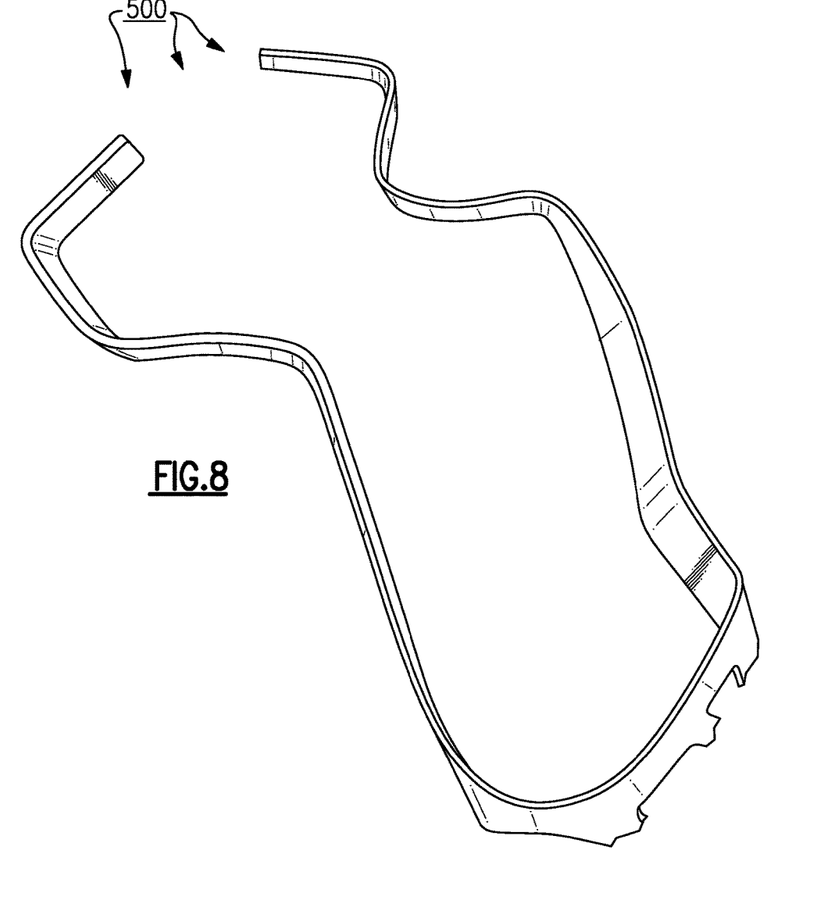
FIG. 8 shows a perspective view of the first embodiment of the sleep apnea headgear as it is being manipulated by a person.

FIGS. 7 and 8 show the versatility facilitated by the use of a metal layer in the headgear fabric 300 to provide clearance from and/or comfort to a patient's face.

Figure 9:
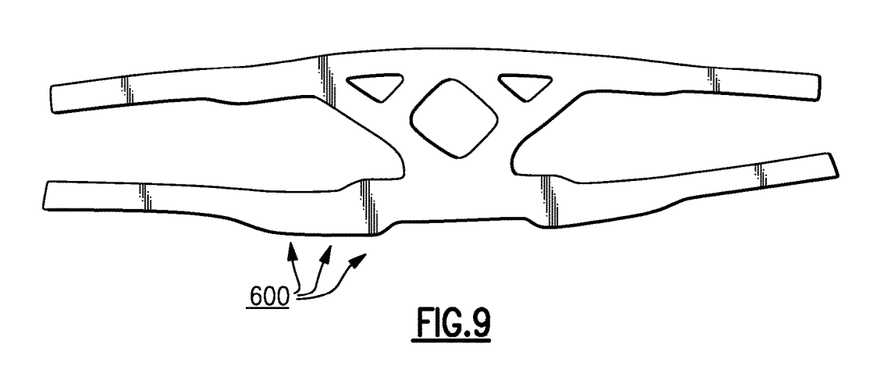
FIG. 9 shows a top orthographic view of the second embodiment of the sleep apnea headgear.
Figure 10:
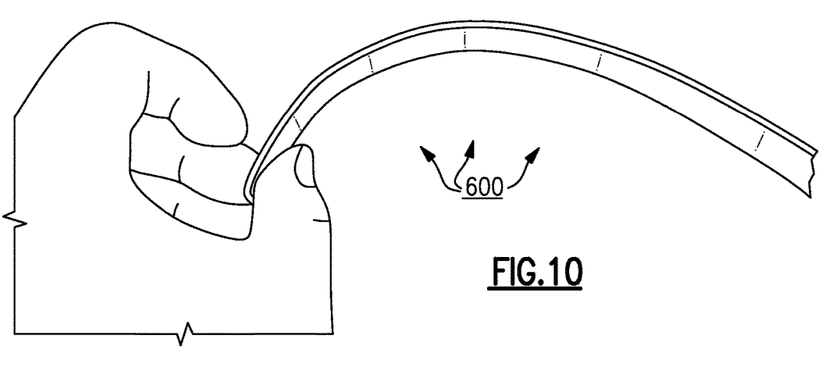
FIG. 10 shows a perspective view of the second embodiment of the sleep apnea headgear as it is being manipulated by a person.
Figure 11:
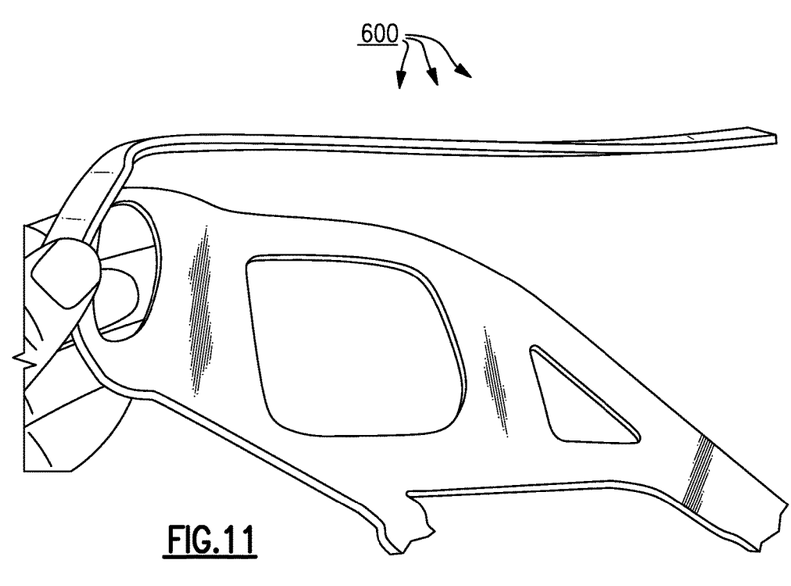
FIG. 11 shows a perspective view of the second embodiment of the sleep apnea headgear as it is being manipulated by a person.

FIGS. 9 to 11 show how a headgear 600 made of fabric 200 and including a rigid plastic layer can be shaped and manipulated to help bring about the advantages described herein.

III. Fabric Forming Processes

Flame lamination can be used to make medical headgear fabrics according to the present invention, but it is not the preferred process. The preferred thermoforming process utilizes a polyurethane (PU) foam and two nylon/spandex blends to form a three layer composite. The PU is fed into one side of the lamination machine at the same one of the fabrics is also fed in. The top surface of the foam is melted by direct flame contact to generate a tacky condition. The melted foam and fabric is then fed through a compression roller to squeeze the two materials together forcing the melted foam into the pores of the fabric. As it cools a bond is formed. This process is then repeated to bond the other fabric. Thermoforming takes previously laminated composites and utilizes a combination of heat (not flame) and pressure to generate permanent shapes and variable height within the composite.

For multi-layered products like the medical headgears of the present invention, the final composite is typically generated by taking two separate two-layer laminate sub-assemblies, inserting the plastic between these sub-assemblies, spraying some adhesive between these layers and then thermoforming the sub-assemblies together. The heat and pressure from the thermoforming process then causes the reaction in the adhesive that parts bonds the subassemblies and inserts together. Thermoforming provides more thickness and softness to the headgear for increased patient comfort. The thermoforming process can be used to make medical headgear fabrics with a plastic layer, such as fabric 200, or fabrics with a metal layer, such as fabric 300.

The fabric and headgear described herein provide all-textile, completely soft and drapable devices that provide comfort and flexibility to the wearer while maintaining stability and control on the wearer's head. The integrity of the fabric and device is provided internally, not externally to add to the comfort of the device. There are no stitches or seams present on the skin-surface side of the fabric. Accordingly, skin irritation is reduced and/or alleviated by the fabric and device described herein.

DEFINITIONS

The following definitions are provided to facilitate claim interpretation and claim construction:

Present invention: means at least some embodiments of the present invention; references to various feature(s) of the "present invention" throughout this document do not mean that all claimed embodiments or methods include the referenced feature(s).

First, second, third, etc. ("ordinals"): Unless otherwise noted, ordinals only serve to distinguish or identify (e.g., various members of a group); the mere use of ordinals implies neither a consecutive numerical limit nor a serial limitation.

Rigid plastic: any plastic layer at least substantially more rigid than foam.

To the extent that the definitions provided above are consistent with ordinary, plain, and accustomed meanings (as generally shown by documents such as dictionaries and/or technical lexicons), the above definitions shall be considered supplemental in nature. To the extent that the definitions provided above are inconsistent with ordinary, plain, and accustomed meanings (as generally shown by documents such as dictionaries and/or technical lexicons), the above definitions shall control. If the definitions provided above are broader than the ordinary, plain, and accustomed meanings in some aspect, then the above definitions shall be considered to broaden the claim accordingly.

To the extent that a patentee may act as its own lexicographer under applicable law, it is hereby further directed that all words appearing in the claims section, except for the above-defined words, shall take on their ordinary, plain, and accustomed meanings (as generally shown by documents such as dictionaries and/or technical lexicons), and shall not be considered to be specially defined in this specification. In the situation where a word or term used in the claims has more than one alternative ordinary, plain and accustomed meaning, the broadest definition that is consistent with technological feasibility and not directly inconsistent with the specification shall control.

Unless otherwise explicitly provided in the claim language, steps in method steps or process claims need only be performed in the same time order as the order the steps are recited in the claim only to the extent that impossibility or extreme feasibility problems dictate that the recited step order (or portion of the recited step order) be used. This broad interpretation with respect to step order is to be used regardless of whether the alternative time ordering(s) of the claimed steps is particularly mentioned or discussed in this document.

What is claimed is:

1. A headgear, comprising:
    a first thermoformed headgear section including:
        a first foam layer;
        a first skin-facing fabric layer configured to contact a user's skin; and
        a first outer fabric layer;
    a second thermoformed headgear strap section connected to the first thermoformed headgear section, the second thermoformed headgear strap section including:
        a second skin-facing fabric layer configured to contact a user's skin;
        a second outer fabric layer;
        a second foam layer located between the second skin-facing fabric layer and the second outer fabric layer, the second foam layer having an outer surface; and a layer of rigid material located between the second skin-facing fabric layer and the second outer fabric layer, and adjacent the second foam layer such that the layer of rigid material is in contact with the outer surface of the second foam layer; and a joint to connect the first thermoformed headgear section to the second thermoformed headgear strap section, wherein each of the first thermoformed headgear section and the second thermoformed headgear strap section forms a unitary laminate structure, and wherein the second thermoformed headgear strap section is configured to be attached to a face mask assembly.

2. The headgear of claim 1, wherein the rigid material comprises plastic, metal, ceramic or composite material.

3. The headgear of claim 1 wherein the first foam layer is located between the first skin-facing fabric layer and the first outer fabric layer.

4. The headgear of claim 1, wherein each of the first skin-facing fabric layer and the second skin-facing fabric layer comprises a soft, stretchable fabric.

5. The headgear of claim 1, wherein each of the first outer fabric layer and the second outer fabric layer comprises a knit fabric.

6. The headgear of claim 1, wherein each of the first skin-facing fabric layer, the second skin-facing fabric layer, the first outer fabric layer and the second outer fabric layer comprises a soft nylon fabric.

7. The headgear of claim 1, wherein each of the unitary laminate structure of the first thermoformed headgear section and the unitary laminate structure of the second thermoformed headgear strap section comprises a seam on a respective one of the first outer fabric layer and the second outer fabric layer, and wherein each of the first skin-facing fabric layer and the second skin-facing fabric layer is seamless.

8. The headgear of claim 1, wherein the layer of rigid material has an outer surface extending in parallel with the outer surface of the second foam layer, and the outer surface of the layer of rigid material is in contact with the outer surface of the second foam layer.

9. The headgear of claim 1, wherein the first foam layer, the first skin-facing fabric layer and the first outer fabric layer are thermoformed to form the unitary laminate structure of the first thermoformed headgear section.

10. The headgear of claim 1, wherein the second foam layer, the second skin-facing fabric layer and the second outer fabric layer are thermoformed to form the unitary laminate of the second thermoformed headgear strap section.

11. The headgear of claim 1, wherein the second thermoformed headgear strap section is configured to be attached directly to the face mask assembly.

12. The headgear of claim 2, wherein the composite material comprises a fiber reinforced composite material.

13. The headgear of claim 2, wherein the metal comprises aluminum.

14. The headgear of claim 2, wherein the plastic material comprises a thermoplastic material.

15. The headgear of claim 14, wherein the thermoplastic material comprises a polyamide.

16. The headgear of claim 15, wherein the polyamide comprises a nylon 6 or nylon 12.

17. A headgear device comprising:

a crown section configured to extend over and/or around a crown of a user's head; and a strap section connected to the crown section;

wherein each of the crown section and the strap section comprises a skin-facing fabric layer configured to contact the user's skin, an outer fabric layer, and a foam layer located between the skin-facing fabric layer and the outer fabric layer, the foam layer having an outer surface; and wherein the strap section further comprises a layer of rigid material located between the fabric layers and adjacent the foam layer such that the layer of rigid material is in contact with the outer surface of the foam layer, wherein each of the crown section and the strap section forms a unitary laminate structure, and wherein the strap section is configured to be attached to a face mask assembly.

18. The headgear device of claim 17, wherein each of the skin-facing fabric layers and the outer fabric layers comprises a soft, stretchable fabric.

19. The headgear device of claim 17, wherein each of the skin-facing fabric layers and the outer fabric layers comprises a soft nylon fabric.

20. The headgear device of claim 17, wherein the layer of rigid material has an outer surface extending in parallel with the outer surface of the foam layer, and the outer surface of the rigid material is in contact with the outer surface of the foam layer.

21. The headgear device of claim 17, wherein the strap section is configured to be attached directly to the face mask assembly.

22. The headgear device of claim 17, wherein the rigid material comprises plastic, metal, ceramic or composite material.

23. The headgear device of claim 22, wherein the composite material comprises a fiber reinforced composite material.

24. The headgear device of claim 22, wherein the metal comprises aluminum.

25. The headgear device of claim 22, wherein the plastic material comprises a thermoplastic material.

26. The headgear device of claim 25, wherein the thermoplastic material comprises a polyamide.

27. The headgear device of claim 26, wherein the polyamide comprises a nylon 6 or nylon 12.

* * * * *